United States Patent
Byun et al.

(10) Patent No.: US 6,245,753 B1
(45) Date of Patent: Jun. 12, 2001

(54) AMPHIPHILIC POLYSACCHARIDE DERIVATIVES

(75) Inventors: Youngro Byun; Yong-Kyu Lee, both of Kwangju (KR)

(73) Assignee: Mediplex Corporation, Korea, Seoul (KR)

( * ) Notice: Subject to any disclaimer, the term of this patent is extended or adjusted under 35 U.S.C. 154(b) by 0 days.

(21) Appl. No.: 09/300,173

(22) Filed: Apr. 27, 1999

(30) Foreign Application Priority Data

May 28, 1998 (KR) ........................................... 19469

(51) Int. Cl.$^7$ ................................................ A61K 31/727
(52) U.S. Cl. ................................ 514/56; 514/54; 514/57; 536/21; 536/17.5; 536/56; 536/92; 536/95; 536/122; 536/123.1; 606/228; 606/231; 604/890.1; 604/891.1
(58) Field of Search ................................. 514/54, 56, 57; 536/21, 17.5, 56, 92, 95, 122, 123.1; 606/228, 231; 604/890.1, 891.1

(56) References Cited

U.S. PATENT DOCUMENTS

| | | | |
|---|---|---|---|
| 4,857,602 | * | 8/1989 | Casey et al. ........................ 525/408 |
| 5,840,387 | * | 11/1998 | Berlowitz-Tarrant et al. ... 418/36.91 |
| 5,855,618 | * | 1/1999 | Patnaik et al. ........................ 623/11 |

OTHER PUBLICATIONS

A. Leone–Bay, et al.; 4–[4–(2–Hydroxybenzoyl)amino]phenyl butyric Acid as a Novel Oral Delivery Agent for Recombinant Human Growth Hormone, 39 J. Med. Chem. 2571–2578 (1996).
R. Altman, et al.; Oral Anticoagulant Treatment with and without Aspirin, 74(1) F.K. Schattauer Verlagsgesellschaft mbH (Stuttgart) 506–510 (1995).
B. Koefoed, et al., Effect of Fixed Minidose Warfarin, Conventional Dose Warfarin and Aspirin on INR and Prothrombin Fragment 1+2 in Patents with Atrial Fibrillation, 77 (5) F.K. Schattauer Verlagsgesellschaft mbH (Stuttgart) 845–848 (1997).
P. Klement, et al., Hirudin causes more bleeding than heparin in a rabbit ear bleeding model, 132 J. Lab Clin Med 181–185 (1998).
R. Hull, et al.; Hirudin versus heparin and low–molecular-weight heparin: And the winner is . . . , 132 J. Lab Clin Med 151–174 (1998).
G. E. Raskob, Msc. Low molecular weight heparin, heparin, and wafarin, 2 Current Opinion in Hematology 372–379 (1995).
L. Wallentin, Unstable coronary artery disease—need for long term antithrombotic treatment, Aspirin alone is not sufficient, I would associate an anticogulant, 33 Cardiovacular Research 292–294 (1997).

S. Milstein, et al., Partially unfolded proteins efficiently penetrate cell membranes—implications for oral drug delivery; 53 Journal of Controlled Release 259–267 (1998).
A. Leone–Bay, et al, The evolution of an oral heparin dosing solution, 22(8) Drugs of the Future 885–891 (1997).
A. Leone–Bay, et al., Oral Delivery of Sodium Cromolyn: Preliminary Studies In Vivo and In Vitro, 13(2) Pharmaceutical Research 222–226 (1995).
A. Leone–Bay, et al., N–Acylated α–Amino Acids as Novel Oral Delivery Agents for Proteins, 38 J. Med. Chem. 4263–4269 (1995).
E. Windsor & G. Cronheim, Gastro–Intestinal Absorption of Heparin and Synthetic Heparinoids, 190 Nature 263–264 (1961).
A. Leone–Bay, et al., Acylated non–α–amino acids as novel agents for the oral delivery of heparin sodium, USP, 50 Journal of Controlled Release 41–49 (1998).
D. Brayden, et al., Heparin Absorption Across the Intestine: Effects of Sodium N–[8–(2–Hydroxybenzoyl) Amino] Caprylate in Rat In Situ Intestinal Installations and in Caco–2 Monolayers, 14(12) Pharmaceutical Research 1772–1779 (1997).
A. Leone–Bay, et al., Synthesis and Evaluation of Compounds That Facilitate the Gastrointestinal Absorption of Heparin, 41 J. Med. Chem 1163–1171, (1998).
A. Leone–Bay, et al., Microsphere Formation in a Series of Derivatized α–Amino Acids: Properties, Molecular Modeling, and Oral Delivery of Salmon Calcitonin, 38 J. Med. Chem 4257–4262 (1995).
Diancourt et al. *Journal of Bioactive and Compatible Polymers* Jul. 1996, 11(3), 203–218.*

* cited by examiner

Primary Examiner—Kathleen K. Fonda
(74) Attorney, Agent, or Firm—Clayton, Howarth & Cannon, P.C.

(57) ABSTRACT

Polysaccharides, which are widely used as an anticoagulation drugs, especially heparin, are clinically administered only by intravenous or subcutaneous injection because of their strong hydrophilicity and high negative charge. Amphiphilic heparin derivatives were synthesized by conjugate to bile acids, sterols, and alkanoic acids, respectively. The hydrophobicity of the heparin derivatives depended on the feed mole ratio of heparin to hydrophobic agent. The heparin derivatives were slightly hydrophobic and exhibited good solubility in a water-acetone solvent, as well as water. The heparin derivatives have a high anticoagulant activity. These slightly hydrophobic heparin derivatives can be absorbed in gastric intestinal tract and can be used as oral dosage form. Also, the heparin derivatives can be used for the surface modification to prevent anticoagulation for medical devices such as extracorporeal devices and implanted devices.

22 Claims, 2 Drawing Sheets

US 6,245,753 B1

AMPHIPHILIC POLYSACCHARIDE DERIVATIVES

BACKGROUND OF THE INVENTION

This invention relates to polysaccharide derivatives having increased hydrophobicity as compared to the unmodified polysaccharide. More particularly, the invention relates to amphiphilic polysaccharide derivatives, such as amphiphilic heparin derivatives, wherein the bioactivity of the polysaccharide is preserved. Further, the invention relates to methods of making and using such amphiphilic polysaccharide derivatives.

Heparin is a polysaccharide composed of sulfated D-glucosamine and D-glucuronic acid residues. Due to its numerous ionizable sulfate groups, heparin possesses a strong electronegative charge. It is also a relatively strong acid that readily forms water-soluble salts, e.g. heparin sodium. It is found in mast cells and can be extracted from many body organs, particularly those with abundant mast cells. The liver and lungs are especially rich in heparin. The circulating blood contains no heparin except after profound disruption of mast cells. Heparin has many physiological roles, such as blood anticoagulation, inhibition of smooth muscle cell proliferation, and so forth. In particular, heparin is a potent anticoagulant agent that interacts strongly with antithrombin III to prevent the formation of fibrin clots. In vivo, however, applications of heparin are very limited. Because of its hydrophilicity and high negative charge, heparin is not absorbed efficiently from the GI tract, nasal or buccal mucosal layers, and the like. Therefore, the only routes of administration used clinically are intravenous and subcutaneous injections. Moreover, since heparin is soluble in relatively few solvents, it is hard to use for coating surfaces of medical devices or in delivery systems.

To improve the properties of heparin, R. J. Linhardt et al., 83 J. Pharm. Sci. 1034–1039 (1994), coupled lauryl ($C_{12}$) and stearyl ($C_{18}$) groups to single heparin chains, resulting in a derivatized heparin having increased hydrophobicity but with low anticoagulant activity. This result demonstrated that coupling a small linear aliphatic chain to heparin was ineffective in enhancing the hydrophobicity of heparin while preserving activity. Thus, known heparin derivatives have been ineffective in preserving anticoagulation activity.

Rivera et al., Oral Delivery of Heparin in Combination with Sodium N-[8-(2-Hydroxybenzolyl)amino]caprylate: Pharmacological Considerations, 14 Pharm. Res. 1830–1834 (1997), disclosed the possibility of oral delivery of heparin using heparin mixed with sodium N [8-(2-hydroxybenzolyl)amino]caprylate. Dryjski et al., Investigations on Plasma Activity of Low Molecular Weight Heparin after Intravenous and Oral Administrations, 28 Br. J. Clin. Pharma. 188–192 (1989), described the possibility of oral absorption of low molecular weight heparin using enhancers.

Two basic methods have been developed for the formulation of a heparin-releasing system. One method involves binding heparin to a cationic polymer matrix by ionic bonds. The release of heparin is controlled by an ion exchange mechanism. Another method involves dispersed heparin, where heparin is first physically blended with a polymer, and then the release of heparin is controlled by diffusion. The most simple and efficient method for preparing such a heparin device is solvent casting. But a solvent casting method cannot be used for preparing the heparin device since heparin is not dissolved in the organic solvent used for dissolving the polymer. If heparin derivatives could be prepared with increased hydrophobicity while maintaining bioactivity, then the heparin derivatives could be simply immobilized in a polymer matrix by a solvent casting procedure.

In view of the foregoing, it will be appreciated that the development of a hydrophobic heparin derivative or amphiphilic heparin derivative having high bioactivity would be a significant advancement in the art. Such a hydrophobic heparin derivative could be used in a controlled release system, for oral administration, or for surface modification of medical devices for improving biocompatibility. Such a heparin derivative would greatly extend the medical applications of heparin.

BRIEF SUMMARY OF THE INVENTION

It is an object of the present invention to synthesize amphiphilic heparin derivatives having high heparin bioactivity.

It is also an object of the invention to provide a hydrophobic heparin derivative that is soluble in a solvent such as acetone/water, as well as water.

It is another object of the invention to provide heparin derivatives that can be used for a controlled release system to prevent coagulation at a surface.

It is still another object of the invention to provide heparin derivatives that can be absorbed from the GI tract, thereby facilitating oral delivery for preventing blood coagulation.

It is yet another object of the invention to provide heparin derivatives comprising heparin coupled with a bile acid, such as deoxycholic acid or glycocholic acid, or a hydrophobic agent, such as cholesterol, or an alkanoic acid.

These and other objects can be addressed by providing a composition of matter comprising a polysaccharide covalently bonded to a hydrophobic agent. Preferably, the polysaccharide is a member selected from the group consisting of heparin, heparin sodium, sulfonated polysaccharides, cellulose, hydroxymethylcellulose, and hydroxypropylcellulose. An especially preferred polysaccharide is heparin. Preferably, such heparin has a molecular weight of about 200 to 100,000. In a preferred embodiment of the invention, the hydrophobic agent is a member selected from the group consisting of bile acids, sterols, and alkanoic acids. Preferred bile acids include cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof. Preferred sterols include cholestanol, coprostanol, cholesterol, epicholesterol, ergosterol, ergocalciferol, and mixtures thereof. Preferred alkanoic acids comprise about 4 to 20 carbon atoms, such as butyric acid, valeric acid, caproic acid, caprylic acid, capric acid, lauric acid, myristic acid, palmitic acid, stearic acid, and mixtures thereof. Preferably the polysaccharide and the hydrophobic agent are present in a mole ratio of about 1:1 to 1:1000.

Another aspect of the invention comprises a pharmaceutical composition comprising a pharmaceutically effective amount of (a) a composition of matter comprising a polysaccharide covalently bonded to a hydrophobic agent, and (b) a pharmaceutically acceptable carrier. The pharmaceutically acceptable carrier can be an oral drug carrier, sustained release carrier, carrier for parenteral administration, and the like. Preferred sustained release carriers include polymeric matrices such as are well known in the art, including members selected from the group consisting of poly (ethylene oxide)-poly(ε-caprolactone) copolymers, polyurethane polymers, silicone polymers, ethylene vinyl acetate polymers, hydrogels, collagen, gelatin, and mixtures thereof, and the like.

Still another aspect of the invention comprises a method for inhibiting blood coagulation on medical devices that come in contact with blood comprising coating the medical device with a pharmaceutical composition comprising a polymeric matrix intimately admixed with a composition of matter comprising heparin covalently bonded to a hydrophobic agent. Typically, the medical device is coated by using a film casting technique such as is well known in the art.

DETAILED DESCRIPTION

Figure 1:
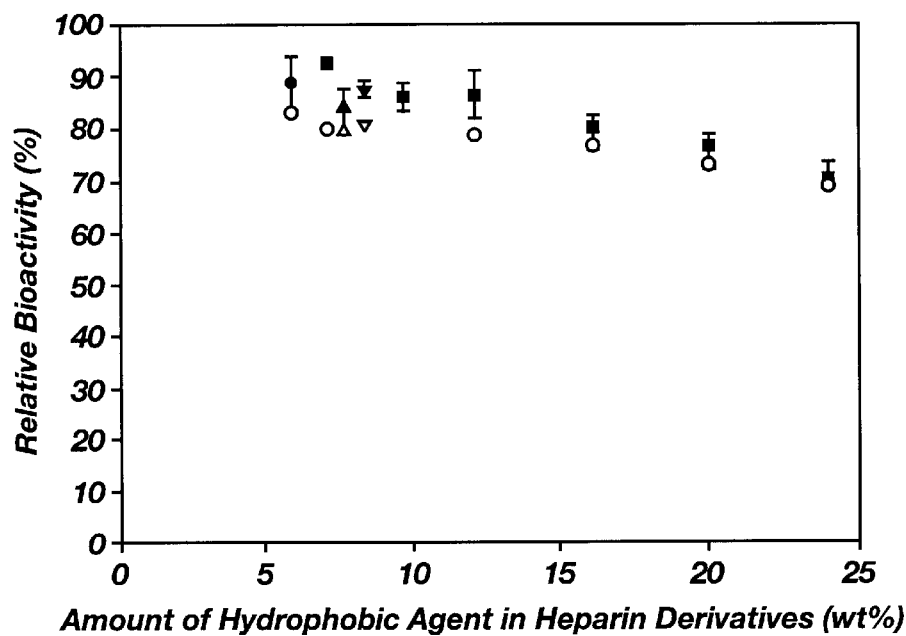
FIG. 1 shows bioactivity of hydrophobic heparin as determined by APTT (closed symbols) and chromogenic (open symbols) assay: ■ and □, deoxycholic acid (DOCA); ● and ○, cholesterol; ▼ and ▽, palmitic acid; ▲ and △, lauric acid.

Before the present amphiphilic polysaccharide composition and methods of making and use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "a bile acid" includes a mixture of two or more of such bile acids, reference to "an alkanoic acid" includes reference to one or more of such alkanoic acids, and reference to "a sterol" includes reference to a mixture of two or more sterols.

In describing and claiming the present invention, the following terminology will be used in accordance with the definitions set out below.

As used herein, "bile acids" means natural and synthetic derivatives of the steroid, cholanic acid, including, without limitation, cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof, and the like.

As used herein, "sterols" means alcohols structurally related to the steroids including, without limitation, cholestanol, coprostanol, cholesterol, epicholesterol, ergosterol, ergocalciferol, and mixtures thereof, and the like.

As used herein, "alkanoic acids" means saturated fatty acids of about 4 to 20 carbon atoms. Illustrative alkanoic acids include, without limitation, butyric acid, valeric acid, caproic acid, caprylic acid, capric acid, lauric acid, myristic acid, palmitic acid, stearic acid, and mixtures thereof, and the like.

As used herein, "hydrophobic heparin derivative" and "amphiphilic heparin derivative" are used interchangeably. Heparin is a very hydrophilic material. Increasing the hydrophobicity of heparin by bonding a hydrophobic agent thereto results in what is termed herein an amphiphilic heparin derivative or hydrophobic heparin derivative. Either term is believed proper because the heparin derivative has increased hydrophobicity as compared to native heparin and the heparin derivative has a hydrophilic portion and a hydrophobic portion and is, thus, amphiphilic.

It is well known that heparin is used as an antithrombogenic agent to prevent blood coagulation. Heparin is highly hydrophilic because of a high density of negative charges such as are provided by sulfonic and carboxylic groups. Due to this hydrophilicity, heparin is usually administered by intravenous or subcutaneous injection. Heparin derivatives with slightly hydrophobic properties or amphiphilic properties and with high bioactivity are described herein. Hydrophobic agents, such as bile acids, e.g. deoxycholic acid (DOCA); sterols, e.g. cholesterol; and alkanoic acids, e.g. lauric acid and palmitic acid, were coupled with heparin. Both deoxycholic acid and cholesterol are non-toxic since they are naturally occurring compounds found in the body. The amine groups of heparin were coupled with carboxyl groups of the hydrophobic agents. The end carboxylic groups in DOCA, lauric acid, and palmitic acid were used directly for the coupling reaction, while the hydroxy group of cholesterol was activated by reaction with chloroacetic acid before coupling. It was determined that conjugating such hydrophobic moieties to the amine groups of heparin had little or no effect on heparin bioactivity. The coupling between heparin and hydrophobic agents was confirmed by detecting the amide bond by FT-IR and $^{13}$C-NMR analysis.

The yield of the coupling reaction was about 70 to 80% and was not significantly changed by changing the hydrophobic agents or feed molar ratios. In the case of the heparin-DOCA conjugate, as the feed ratio was increased, the amount of DOCA in the conjugate was also increased. The weight % of DOCA in heparin-DOCA was 24% when the feed molar ratio of heparin to DOCA was 1:200. This molar ratio was very high compared to the ratio of amine groups in heparin to DOCA. Therefore, this feed ratio is estimated as an excess amount of DOCA.

The hydrophobic heparin derivatives according to the present invention would have many medical applications. For example, the hydrophobic heparin can be administered orally. The oral administration of heparin can extend greatly the usage of heparin as an oral anti-coagulant drug. The heparin derivative is formulated with a pharmaceutically acceptable carrier such as is well known in the art. By way of further example, hydrophobic heparin derivatives can be used as a coating material for medical devices such as catheters, cardiopulmonary bypass circuits, hear lung oxygenators, kidney dialyzers, stent or balloon coating for preventing restenosis, and the like. The hydrophobic heparin derivative is typically mixed with a carrier, and then coated on the surface of the medical device by a film casting technique such as is well known in the art.

After modification, heparin-hydrophobic agents were also found to have a tendency in fast protein liquid chromatography (FPLC®) to exhibit hydrophobic interactions with hydrophobic media, as shown by chromatography on Phenyl Sepharose® (eluting in ammonium sulfate buffer rather than phosphate buffer). These heparin derivatives showed enhanced binding affinity when compared to unmodified heparin. The increased interaction of modified heparin derivatives with Phenyl Sepharose® is attributable to its enhanced hydrophobicity, the result of the hydrophobic functional groups present. These results suggest hydrophobic heparin can be obtained by conjugating a bile acid, sterol, or alkanoic acid to heparin. In solubility tests, polar solvents or organic solvents were suitable to dissolve the heparin-hydrophobic agent conjugates. For example, the heparin-deoxycholic acid conjugate showed good solubility in 65% acetone solution (35% water). Finally, it was determined that bioactivity of modified heparin derivatives was not appreciably influenced by conjugation with hydrophobic agents. The role of a hydrophobic agent conjugated to heparin was studied with respect to two biological activities of heparin as determined by anticoagulation and factor Xa assays. Although hydrophobicity is associated with a somewhat reduced anticoagulant activity and antifactor Xa activity, the decrease of bioactivity was not considered serious. These results indicate that blocking the amine groups of heparin had little effect on its bioactivity. The bioactivity of heparin in heparin-hydrophobic agent conjugates exhibited a progressive reduction, however, when the amount of hydrophobic agent in the conjugate exceeded 20 wt. %. At less than 20 wt. % of hydrophobic agent in the conjugates, the bioactivity of the conjugates was greater than 80% of the bioactivity of unmodified heparin. It is suggested that 80% of bioactivity in hydrophobic heparin is enough to support bioactivity in medical applications.

EXAMPLE 1

Synthesis of Heparin-DOCA Conjugates. Five ml of N-hydroxylsuccinimide (HOSU, 92 mg/5 ml) in dimethylformamide (DMF) was mixed with 5 ml of dicyclohexylcarbodiimide (DCC) (165 mg/5 ml) in DMF, followed by adding 5 ml of DOCA (196 mg/5 ml) in DMF. The mole ratio of DOCA, HOSu, and DCC was 1:1.6:1.6. The concentrations of HOSu and DCC were slightly higher than that of DOCA to activate DOCA completely. The resulting solution was reacted for 5 hours at room temperature under vacuum, and then the byproduct dicyclohexylurea (DCU), which precipitated during the reaction, was removed. The unreacted DCC was removed by adding a drop of distilled water and filtering. The remaining HOSu was also removed by adding 15 ml of distilled water. The activated DOCA was precipitated and then lyophilized. The activated DOCA was then dissolved in DMF and reacted with heparin for 4 hours at room temperature. The amounts of heparin used in such reactions ranged from 40 to 400 mg. After reaction, there were two types of products: a water soluble product and a water-insoluble product. These products were separated by filtration through a 0.45 μm membrane filter, and the water-insoluble product was dried in a vacuum oven. The water-soluble product was dialyzed for 1 day against water using a membrane (MWCO 3,500), and then heparin-DOCA was freeze dried.

The heparin derivatives prepared according to this procedure were characterized by FT-IR and NMR according to methods well known in the art to prove the successful coupling between heparin and the hydrophobic agent. The proof of the heparin derivatives is the amide bond produced by the coupling of an amine group of heparin with a carboxyl group of the hydrophobic agent. In the FT-IR spectrum, significant variation in the spectra was found in the range from 1740 to 1500 $cm^{-1}$. An intense band was observed at 1585 $cm^{-1}$ and assigned to the amide vibrations, which are correlated with the presence of amide bond between heparin and hydrophobic agent. The peak of N—H groups in heparin part of heparin derivative appeared around 3500 ad 1620 $cm^{31\ 1}$, respectively. The $^{13}$C-NMR spectrum of the heparin-DOCA conjugate showed characteristic absorption peaks at δ7.58(carbon at amine bond), 5.5(H-1 of glucosamine 2,6-disulfate), δ5,35(H-1 of glucosamine 2-sulfate), δ5.2(H-1 of iduronic acid 2-sulfate). $^{13}$C-NMR spectra in a comparison of heparin-DOCA and heparin showed different peaks at 178 ppm (carbon at amine bond). These results confirm the presence of an amide bond in the heparin-DOCA conjugate, demonstrating the coupling of an amine group of heparin to a carboxyl group of DOCA.

EXAMPLE 2

Preparation of Heparin-Cholesterol Conjugates. The hydroxyl group of cholesterol was activated by reaction with chloroacetic acid to result in a free carboxyl group. The modified cholesterol was reacted with HOSu and DCC in 10 ml of DMF. The mole ratio of cholesterol, HOSu, and DCC was 1:1.6:1.6 and reaction was for 5 hours at room temperature. To remove the unreacted DCC and HOSu, water was added and the solution was filtered with a 0.45 μm membrane. Next, the activated cholesterol was reacted with heparin solution for 4 hours. Two products, a water-soluble product and a water-insoluble product, were obtained from the reaction. These products were treated according to the procedure described above in Example 1.

EXAMPLE 3

Synthesis of Heparin-Alkanoic Acid Conjugates. Lauric acid and palmitic acid were coupled to heparin according to the procedure of Example 1. The carboxyl group of the alkanoic acids were coupled with amine groups of heparin to form amide bonds. Coupling agents were also HOSu and DCC.

For heparin-DOCA, heparin-cholesterol, and heparin-alkanoic acid, the production yield, molecular weight, and binding mole ratios between heparin and hydrophobic agents varied according to the mole ratio of reactants. The yield of heparin-DOCA conjugates was in the range from 71 to 77%. The molecular weight of heparin was determined as 12,386 daltons by light scattering. The amount of hydrophobic agent in modified heparin derivatives was calculated by subtracting the heparin molecular weight from the measured molecular weight of each heparin derivative. As the feed mole ratio of deoxycholic acid to heparin was increased from 1:6 to 1:200, the amount of DOCA in heparin-DOCA conjugates was increased from 7 to 24%. For the heparin-cholesterol conjugates, the yield also was in the range from 73 to 78%. The amount of cholesterol in such hydrophobic heparin conjugates, however, was slightly lower than the amount of DOCA in heparin-DOCA conjugates. In heparin-lauric acid and heparin-palmitic acid conjugates, similar amounts of alkanoic acid were coupled to heparin.

EXAMPLE 4

Solubility Test of Heparin-DOCA Conjugate. Heparin can be dissolved in relatively few solvents, such as water and formamide. The heparin derivatives of the present invention have a slightly hydrophobic property, thus it was anticipated that such derivatives would be soluble in additional solvents. This was tested in the present example by assessing solubility in mixtures of acetone and water as the solvent. In the case of heparin-DOCA conjugates, as the wt.% of DOCA increased, the solubility of the conjugate in the solvent was increased. In the case of 14 wt % of DOCA, the heparin-DOCA conjugate was dissolved in 50:50 acetone-water, but the conjugate was not dissolved in 70:30 acetone-water. In the case of 24 wt % of DOCA, the solubility of the heparin-DOCA conjugate in the solvent was increased as the acetone content of the solvent was increased. The solubility of heparin-DOCA (24%) in the solvent was maximized at 50:50 volume ratio of acetone and water.

EXAMPLE 5

Analysis on Separation of Heparin on Phenyl-Sepharose CL-4B Gel at 4° C. Phenyl-Sepharose® CL-4B was used for removing the unreacted heparin from heparin-DOCA, heparin-cholesterol, and heparin-alkanoic acid. In addition, it was useful for estimating the degree of hydrophobicity in coupled heparin derivatives. A commercial heparin sodium preparation from beef lung (anticoagulant activity, 140 USP units per mg) was obtained from Pharmacia Hepar Co. (Franklin, Ohio). A Phenyl Sepharose CL-4B gel column was obtained from Pharmacia Biotech (Sweden). The column (HR 16/30 I.D.) was washed with ten volumes of water and then was equilibrated before use by washing with at least 40 ml of 50 mM phosphate buffer pH 7.0 for 20 minutes followed by 40 ml of 50 mM phosphate buffer pH 7.0 containing 1.7 M ammonium sulfate and then 40 ml of 50 mM phosphate buffer pH 7.0. The solution of heparin (5 mg) and hydrophobic heparin (5 mg) in the same phosphate buffer (5 ml) was loaded on the column, and eluted with the gradient solvent respectively. The flow rate was 1 ml/min, and each 2-ml fraction was collected by fraction collector. After elution on the column, the column was washed with 100 ml of water and 1.7 M ammonium sulfate to remove all of the heparin or heparin-DOCA conjugates retained, and the collected fractions were mixed with Azure A (0.01 mg/ml) for 1 minute. Each fraction that included heparin or hydrophobic heparin was quantified by monitoring the absorbance at 500 nm spectrophotometrically in a Varian CARY 1E UV/VIS spectrometer.

The change in elution curves of heparin-DOCA conjugates in FPLC for the different coupling ratios between heparin and DOCA was observed. Heparin was eluted with PBS as eluent, but not with ammonium sulfate since heparin is very hydrophilic. Heparin-DOCA conjugate was not eluted in PBS but was eluted in ammonium sulfate solution. As the concentration of ammonium sulfate in the eluent increased, the hydrophobicity of the eluted heparin conjugates also increased. The heparin-DOCA conjugate was completely eluted in 1.3 M ammonium sulfate solution, even if the content of DOCA was increased.

EXAMPLE 6

Bioactivity of Heparin Derivatives. Anticoagulant activities of modified heparin derivatives were determined by activated partial thromboplastin time (APTT) and Factor Xa chromogenic assay, respectively. The antithrombogenic activities of the heparin derivatives were measured by FXa chromogenic assay and APTT, respectively (FIG. 1). The bioactivity of heparin used in these experiments had a potency of 140 units per mg. The bioactivities of all of the heparin derivatives prepared in this study was above 70% compared to the bioactivity of unmodified heparin. There was no difference in the bioactivities of the conjugates with respect to the hydrophobic agents used for making the conjugates. The bioactivities of heparin derivatives decreased slightly, however, with increasing amounts of hydrophobic agent in the conjugates. When a conjugate containing 7 wt % of DOCA was tested, the relative bioactivity of the heparin-DOCA conjugate was 93% according to the APTT assay and 80% by the FXa assay. In contrast, when a conjugate containing 24 wt % DOCA was tested, the relative bioactivity of such heparin-DOCA conjugate decreased to 71.5% (APTT) and 70.1% (FXa assay).

EXAMPLE 7

Heparin Oral Delivery. Six rats, housed in the animal care facility at the Korea Animal Center were fasted for 12 hours before dosing. Groups of rats weighing 250–300 g were administered a single oral dose of heparin, high molecular weight heparin-DOCA, or low molecular weight heparin-DOCA. Blood samples (0.5 ml) were collected serially by heparin coated capillary mixed with 3.8% sodium citrate. Samples were collected prior to administration of heparin or heparin derivatives and for 10 hours thereafter at hourly intervals. Plasma was harvested by centrifugation and was frozen at below −20° C. Plasma heparin activity in each sample was determined by APTT assays. The APTT bioassay was performed according to the procedure of Example 6. Plasma APTT units were determined from clotting time, which was measured by fibrometer.

Figure 2:
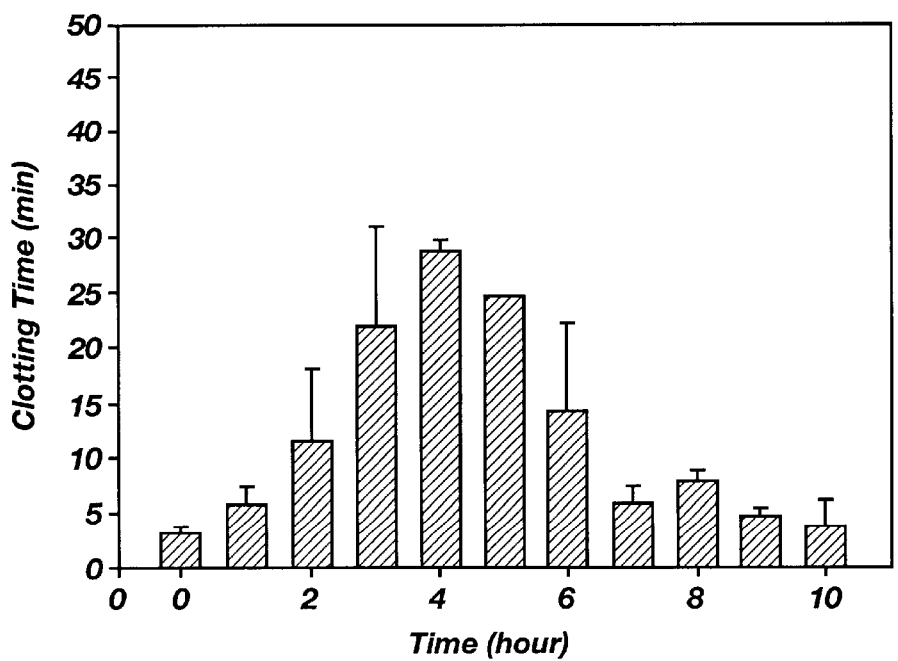
FIG. 2 shows clotting time as a function of time when low molecular weight heparin-DOCA is administered orally.
Figure 3:
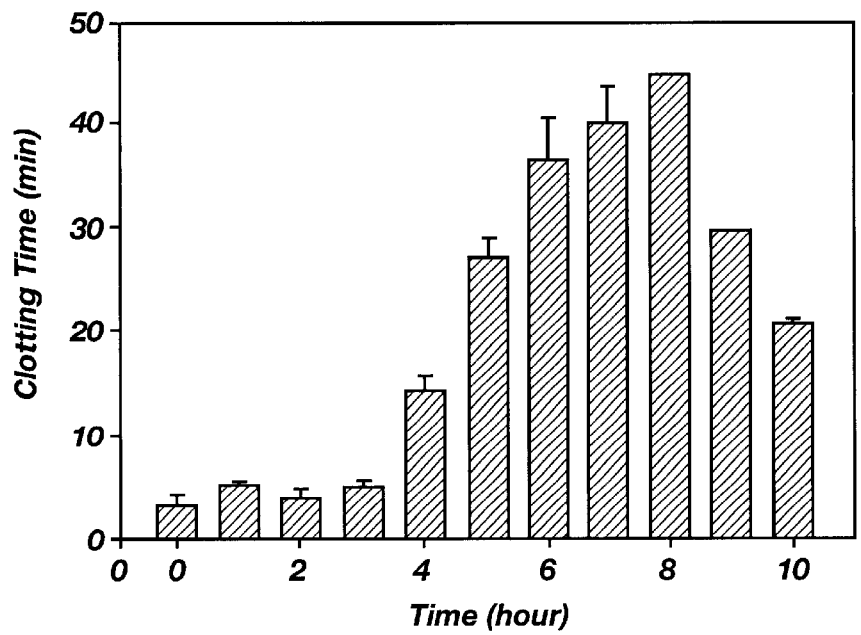
FIG. 3 shows clotting time as a function of time when high molecular weight heparin-DOCA is administered orally.

In the case of low molecular weight heparin-DOCA (FIG. 2), the maximum clotting time occurred at 4 hours after orally administering. The clotting time was back to the baseline after 10 hours. For the high molecular weight heparin-DOCA (FIG. 3), the maximum clotting time occurred at 8 hours after oral administering. The clotting time was maintained above 20 minutes after 10 hours. The high molecular weight heparin-DOCA had higher anticoagulant activity than low molecular weight heparin-DOCA.

EXAMPLE 8

Release Rate of Heparin Derivatives in Vitro. In vitro studies were performed by first casting derivatized heparin in a PEO/PCL multiblock copolymer over polyethylene discs (2.22 cm diameter). PEO/PCL is a multiblock copolymer composed of alternating blocks of poly(ethylene oxide) (Mw about 2,000) and poly(ε-caprolactone) (MW about 2,000), wherein the total molecular weight of the copolymer is about 30,000. The heparin derivative was mixed with the polymer, dissolved in acetone/water, cast on the polyethylene discs, and then the solvent evaporated. The lower sides of the discs were then attached to the bottom of a 50-ml vial. Each disc was immersed in 20 ml of PBS buffer (pH 7.4, I=0.15) and placed at a randomly allocated position in a shaking water bath (Han Baek Scientific Co., Korea) at 37° C. and 80 rpm. At selected times, determined so that the heparin derivatives concentration in the release medium would not exceed 10% of its saturated solubility at 37° C., samples were removed and assayed for drug content by UV spectroscopy (530 nm) after mixing with azure A. At each sampling time the entire release medium was removed and replaced with fresh pre-warmed PBS buffer. Following the release study, the initial amount of heparin derivative in the PEO/PCL multiblock copolymer film was calculated by summation of the cumulative amount released over 40 days, and the amount remaining in the disc at 40 days. This was compared with the initial amount calculated from the drug loading. The cumulative amount of heparin derivative released was plotted against time and the percentages released were used in statistical comparisons performed by repeated measures analysis of variance.

Figure 4:
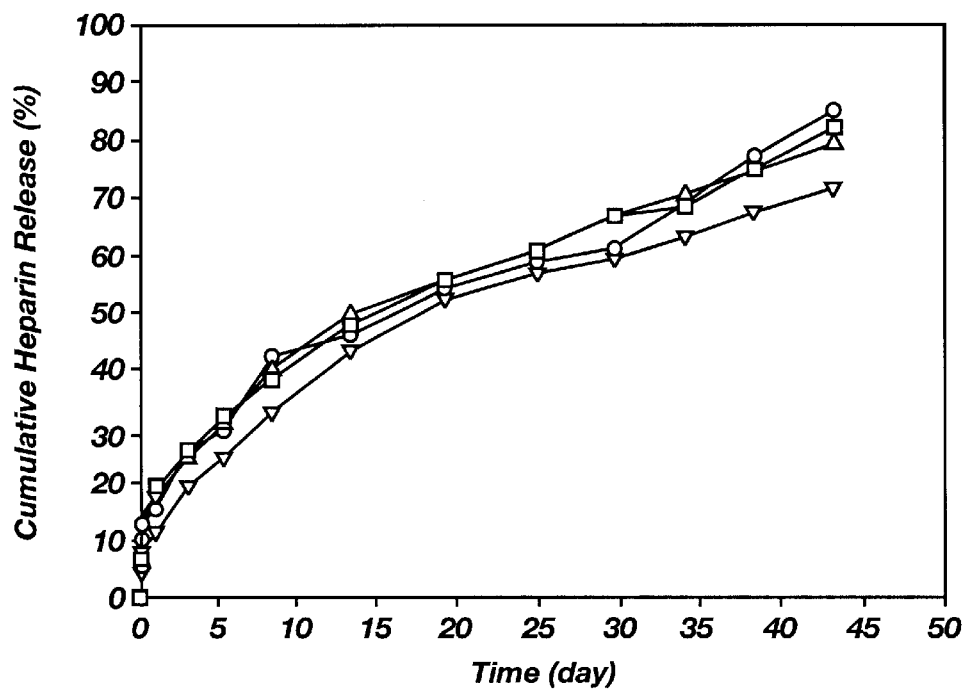
FIG. 4 shows cumulative heparin-DOCA conjugate release from a poly(ethylene oxide)-poly(ε-caprolactone) (PEO-PCL) polymeric matrix as a function of time; the weight % of heparin-DOCA in the polymeric matrix: (▽), 5% DOCA; (○), 10% DOCA; (△), 20% DOCA; (□), 30% DOCA.

The heparin derivatives were released from the polymeric matrix with almost controlled release rate with a small burst effect. The burst effect was shown within 1 hour, and the released amount at the burst was about 10% of the loaded amount of drug (FIG. 4).

What is claimed is:

1. A composition of matter comprising a polysaccharide covalently bonded to a hydrophobic agent, wherein said hydrophobic agent is a member selected from the group consisting of sterols, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

2. The composition of matter of claim 1 wherein the polysaccharide is a member selected from the group consisting of heparin, heparin sodium, sulfonated polysaccharides, cellulose, hydroxymethylcellulose, and hydroxypropylcellulose.

3. The composition of matter of claim 2 wherein said polysaccharide is heparin.

4. The composition of matter of claim 3 wherein said heparin has a molecular weight of about 200 to 100,000.

5. A composition of matter comprising heparin covalently bonded to a sterol, wherein the sterol is a member composition of matter of claim 3 wherein said hydrophobic agent is selected from the group consisting of cholestanol, coprostanol, cholesterol, epicholesterol, ergosterol, ergocalciferol, and mixtures thereof.

6. The composition of matter of claim 1 wherein said polysaccharide and said hydrophobic agent are present in a mole ratio of about 1:1 to 1:1000.

7. A pharmaceutical composition comprising (a) a pharmaceutically effective amount of a composition of matter comprising a polysaccharide covalently bonded to a hydrophobic agent, wherein the hydrophobic agent is a member selected from the group consisting of sterols, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxvcholic acid, dehydrocholic acid, hyocholic acid, hyodeoxycholic acid, and mixtures thereof and (b) a pharmaceutically acceptable carrier.

8. The pharmaceutical composition of claim 7 wherein said pharmaceutically acceptable carrier is an oral drug carrier.

9. The pharmaceutical composition of claim 8 wherein said pharmaceutically acceptable carrier is a sustained release carrier.

10. The pharmaceutical composition of claim 9 wherein said sustained release carrier is a polymeric matrix.

11. The pharmaceutical composition of claim 10 wherein said sustained release carrier is a polymeric matrix selected from the group consisting of poly(ethylene oxide)-poly($\epsilon$-caprolactone)copolymers, polyurethane polymers, silicone polymers, ethylene vinyl acetate polymers, hydrogels, collagen, gelatin, and mixtures thereof.

12. The pharmaceutical composition of claim 11 wherein said polymeric matrix is a poly((ethylene oxide)-poly($\epsilon$-caprolactone) copolymer.

13. The pharmaceutical composition of claim 7 wherein said polysaccharide is heparin.

14. A method for inhibiting blood coagulation on a medical device that comes in contact with blood comprising coating said medical device with a pharmaceutical composition comprising a polymeric matrix intimately admixed with a composition of matter comprising heparin covalently bonded to a hydrophobic agent, wherein the hydrophobic agent is a member selected from the group consisting of sterols, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

15. The method of claim 14 wherein said polymeric matrix is a member selected from the group consisting of poly(ethylene oxide)-poly($\epsilon$-caprolactone) copolymers, polyurethane polymers, silicone polymers, ethylene vinyl acetate polymers, hydrogels, collagen, gelatin, and mixtures thereof.

16. The composition of matter of claim 1 wherein the hydrophobic agent is deoxycholic acid.

17. The pharmaceutical composition of claim 7 wherein the hydrophobic agent is a sterol selected from the group consisting of cholestanol, coprostanol, cholesterol, epicholesterol, ergosterol, ergocalciferol, and mixtures thereof.

18. The pharmaceutical composition of claim 7 wherein the hydrophobic agent is deoxycholic acid.

19. The pharmaceutical composition of claim 13 wherein the hydrophobic agent is a sterol selected from the group consisting of cholestanol, coprostanol, cholesterol, epicholesterol, ergosterol, ergocalciferol, and mixtures thereof.

20. The pharmaceutical composition of claim 13 wherein the hydrophobic agent is deoxycholic acid.

21. The method of claim 14 wherein the hydrophobic agent is a sterol selected from the group consisting of cholestanol, coprostanol, cholesterol, epicholesterol, ergosterol, ergocalciferol, and mixtures thereof.

22. The method of claim 14 wherein the hydrophobic agent is deoxycholic acid.

* * * * *

UNITED STATES PATENT AND TRADEMARK OFFICE
CERTIFICATE OF CORRECTION

PATENT NO.    : 6,245,753 B1
DATED         : June 12, 2001
INVENTOR(S)   : Youngro Byun et al.

It is certified that error appears in the above-identified patent and that said Letters Patent is hereby corrected as shown below:

<u>Title page,</u>
Item [57], ABSTRACT,
Lines 5-6, delete "conjugate" and replace with -- conjugation --;
Line 13, insert -- the -- before "gastric;";
Line 14, delete "form" and substitute -- forms --;
Line 15, delete "the" before "surface.".

<u>Column 6,</u>
Line 11, delete "ad 1620 cm$^{31\ 1}$" and replace with -- and 1620 cm$^{-1}$ --.

<u>Column 9,</u>
Lines 31-33, delete "composition of matter of claim 3 wherein said hydrophobic agent;".
Line 47, delete "glycochenodeoxvcholic" and substitute -- glycochenodeoxycholic --.

<u>Column 10,</u>
Lines 1-11, delete "poly((ethylene oxide)-poly(∈-caprolactone)" and substitute
-- poly(ethylene oxide)-poly(∈-caprolactone) --.

Signed and Sealed this

Fourth Day of October , 2005

JON W. DUDAS
*Director of the United States Patent and Trademark Office*